United States Patent [19]

Fishman et al.

[11] Patent Number: 4,873,076
[45] Date of Patent: Oct. 10, 1989

[54] METHOD OF SAFELY PROVIDING ANESTHESIA OR CONSCIOUS SEDATION

[75] Inventors: Jack Fishman, Miami, Fla.; John Arnold, Fairway, Kans.; Fred Sherman, Hollywood; Jane Hsiao, Copper City, Fla.

[73] Assignee: Baker Cummins Pharmaceuticals, Inc., Miami, Fla.

[21] Appl. No.: 333,321

[22] Filed: Apr. 6, 1989

Related U.S. Application Data

[63] Continuation-in-part of Ser. No. 188,512, Apr. 29, 1988, abandoned.

[51] Int. Cl.$^4$ ............... A61K 31/44; A61K 31/55; A61K 31/445; A61K 47/00
[52] U.S. Cl. ............................ 424/10; 514/220; 514/221; 514/282; 514/329; 514/330; 514/922
[58] Field of Search ............... 514/221, 922, 816, 220, 514/282, 329, 330; 424/10

[56] References Cited

PUBLICATIONS

Nilsson et al., Acta Anaesthesiol Scand. 1986: 30:66–69.
Craig et al., Modern Pharmacology ©1982, 1st. ed. p. 566.
Heilman et al., Research Comm. in Chem. Path & Pharm. vol. 13, No. 4 (4/76), pp. 635–647.
Avery's Drug Treatment, 3rd ed., 1987, pp. 318–319 and 350.
Sawynok et al., Life Sci., 25:1621–1632 (1979).
Jordan et al., Anesthesiology, 53:293–298 (1980).
Billingsley et al., Life Sci., 22:897–906 (1978).
Gylys et al., Fed. Proc., 38:863 (1979).
Bell, J. Pediatrics, 87:803–804 (1975).
Patschke et al., Br. J. Anesth., 49:525 (1977).
Forster et al., Anesth. Analg., 62:920–924 (1983).

Primary Examiner—Douglas W. Robinson
Assistant Examiner—Raymond J. Henley, III
Attorney, Agent, or Firm—Kirschstein, Ottinger, Israel & Schiffmiller

[57] ABSTRACT

A method of inducing anesthesia or conscious sedation while avoiding serious hypotensive episodes comprising the administration of a parenterally active benzodiazpine in conjunction with an opiate analgesic followed by the parenteral administation of from about 1 to about 3 mg of a long-acting pure narcotic antagonist. The antogonist may be administered during the time interval commencing immediately prior to the procedure and continuing until about 3–5 hours after administration of the opiate-benzodiazepine combination.

13 Claims, No Drawings

METHOD OF SAFELY PROVIDING ANESTHESIA OR CONSCIOUS SEDATION

CROSS REFERENCE TO RELATED APPLICATION

This application is a continuation-in-part of application Ser. No. 07/188,512, filed Apr. 29, 1988 now abandoned.

BACKGROUND OF THE INVENTION

1. Field of the Invention

The invention relates to methods of inducing anesthesia or conscious sedation by administration of benzodiazepines in combination with opiate analgesics.

2. Description of the Prior Art

Combinations of opiate analgesics, e.g., fentanyl or meperidine, and benzodiazepines such as diazepam and midazolam, are commonly administered prior to the performance of certain surgical and exploratory procedures, including, e.g., gastric endoscopies and colonoscopies. It has long been known that such combinations can induce respiratory depression, as can benzodiazepines administered alone by the intravenous route. It has also been known that opiates and benzodiazepines produce significant hypotension in many subjects when administered parenterally, although such hypotension is rarely life-threatening when each agent is administered independently.

Pure narcotic antagonists of the naloxone type are highly effective in reversing the untoward side effects of opiate analgesics, including hypotension. However, considerably higher doses of naloxone are required to antagonize opiate-induced hypotension than other opiate effects, probably because the hypotension is mediated in large measure through delta receptors (see, e.g. J. Holaday, et al., *Life Sciences* 31:2209-2212 (1982)) and naloxone is far more potent on the mu receptor (responsible for opiate analgesia and related effects) than the delta receptor (H. Fields, et al., Nature 284:351-353 (1980)).

Benzodiazepines produce hypotension by a completely different mechanism than opiates—i.e., by central inhibition of sympathetic outflow, with a significant decrease in systemic vascular resistance. Numerous studies demonstrate that both diazepam and midazolam produce modest hypotension when used at their recommended dosages. Benzodiazepines do not, however, bind to opioid receptors.

When benzodiazepines and opiate analgesics are administered in combination, there is often a far greater decrease in blood pressure and cardiac output than desired. In fact, this combination may produce a supraadditive effect on blood pressure.

While this effect has been observed with combinations such as diazepam and morphine (J. Marty, et al., *Anesth. Analg.*, 65:113-119 (1986)), it is particularly severe in the case of opiates administered in combination with intravenous midazolam. Heikkila, et al. noted a decrease in mean arterial blood pressure of up to 32% in patients receiving the combination of intravenous midazolam and fentanyl (see *Anesth. Analg.*, 66:693-696 (1987)). Moreover, a number of recently reported deaths after procedures such as colonoscopies are believed attributable to virtual circulatory collapse following meperidine/midazolam anesthesia.

The unusual feature of this severe fall of blood pressure is that it does not occur at the time of maximum blood levels of benzodiazepine and opiate, but it occurs most often after a substantial time delay when the plasma concentration of benzodiazedpine and opiate have fallen. Thus many subjects will have completed the surgical an diagnostic procedure and some may be released from observation before the circulatory collapse occurs. In one series of observations, the average time to circulatory collapse was 30 minutes post-procedure with several subjects having collapse occurring two to three hours post-procedure.

Although it is known that pure narcotic antagonists can reverse opiate-induced hypotension as well as, to some degree, benzodiazepine-induced hypotension, they have not been administered for the purpose of preventing or ameliorating the severe drop in blood pressure that can be caused by the administration of benzodiazepines in combination with opiates to induce anesthesia or conscious sedation. Any antagonist which may currently be administered following anesthesia with a benzodiazepine-opiate combination is normally intended to reverse sedation and possible respiratory depression, and the dosage level utilized is too small to prevent severe hypotension and possible circulatory collapse. For example, Nilsson, et al., *Acta Anaesth. Scand.*. 30:66-69 (1986) disclose the administration of naloxone subsequent to the induction of anesthesia with a midazolamfentanyl combination in patients undergoing abdominal surgery. But the patients received only 0.1-0.2 mg of naloxone intravenously, far too little to protect against the substantial fall in blood pressure which is often observed after the administration of such a combination.

While Nilsson, et al. claimed that they did not observe a major drop in blood pressure with their patients, this observation (if accurate) probably resulted from the fact that the procedures performed did not call for the type of preparation on the part of the patient, including purging and associated fluid loss, which is commonly called for in the case of colonoscopies and related procedures. It is in the latter cases that the most severe hypotensive episodes have occurred. In addition, the patients studied by Nilsson, et al. were ventilated with oxygen, which is often not the case when patients receive benzodiazepine-opiate combinations in situations where a trained anesthesiologist is not present.

At the present time, no truly safe method of inducing anesthesia or conscious sedation with benzodiazepine-opiate combinations has been developed, particularly in the case of patients undergoing colonoscopies or similar procedures where the risk of a sudden and severe drop in blood pressure after induction of anesthesia is not uncommon.

SUMMARY OF THE INVENTION

It is the object of the present invention to provide a method for inducing anesthesia or conscious sedation through the use of benzodiazepines administered in combination with opiate analgesics while avoiding the risk of severe hypotension associated with the concomitant use of such agents.

In keeping with this object and others that will become apparent hereinafter, the present invention resides in the parenteral (preferably intravenous) administration of a benzodiazepine capable of inducing sedation and antegrade amnesia upon parenteral administration, such as diazepam, midazolam or lorazepam, with the concomitant parenteral administration of an opiate analgesic such as meperidine or fentanyl, followed by the administration of from about 1.0 to about 3.0 mg of a long-acting pure narcotic antagonist, preferably after the medical or surgical procedure requiring the anesthesia is performed. It has been found that the administration of the antagonist in the dosage range indicated following anesthesia acts to prevent the serious hypotensive episodes which have frequently occurred subsequent to such anesthesia.

DETAILED DESCRIPTION OF THE INVENTION

The most commonly used opiate-benzodiazepine combinations for induction of anesthesia or conscious sedation are meperidine-diazepam or meperidine-midazolam. The usual dose range for meperidine-diazepam combinations is 25–75 mg/5–15 mg and for meperidine-midazolam combinations, 25–75 mg/2–8 mg, although the administration of even 140 or 150 mg of meperidine is not uncommon. Fentanyl is also administered in combination with benzodiazepines, as are morphine and sufentanil in some instances.

In accordance with the present invention, patients receiving intravenous opiate-benzodiazepine combinations prior to a surgical or exploratory procedure are subsequently administered from about 1.0 to about 3.0 mg of a long-acting pure narcotic antagonist, and preferably from about 1.5 to about 3.0 mg, during the time interval commencing immediately prior to the procedure and continuing until about 3–5 hours after administration of the opiate-benzodiazepine combination. The antagonist is administered parenterally either as a bolus injection for prophylactic purposes, or in 2 to 5 divided doses, with the first dose preferably given immediately after completion of the procedure and the succeeding doses as required until the patient's blood pressure returns to baseline values. The intravenous route of administration is usually most desirable.

The benzodiazepines useful in the method of the present invention include any agents of that class which are capable of inducing basal sedation or general anesthesia upon parenteral administration and, subsequently, antegrade amnesia. The principal representatives of this class are diazepam, midazolam and lorazepam.

Preferred long-acting pure narcotic antagonists for use in the present invention include nalmefene (6-methylene-6-desoxy-N-cyclopropylmethyl-14-hydroxydihydronormorphine) and naltrexone (N-cyclopropylmethyl-14-hydroxydihydronormorphinone). However, the invention is not limited to the preferred antagonists, but comprehends any long-acting narcotic antagonists that have pure antagonist activity and are effective in alleviating or reversing the hypotensive effect of intravenous opiate-benzodiazepine combinations.

The method of the present invention is of particular importance in view of the recently described life-threatening hypotensive effects of benzodiazepines such as midazolam administered in combination with meperidine. A dose of 2.0 mg of nalmefene administered subsequent to meperidine-midazolam analgesia, either as a bolus or in divided doses, has been found to effectively stabilize the patient's blood pressure and return it to baseline values with no adverse side effects. This finding is surprising in view of the fact that naloxone has been considered of limited effectiveness in antagonizing the hypotensive effects of opiates and benzodiazepines administered separately, requiring far higher doses than traditionally used for narcotic reversal.

The novel method is especially valuable in cases where conscious sedation, i.e. a level of sedation where the patient is sufficiently conscious to respond to express instructions, is to be induced, as it often is in painful, minor surgical or diagnostic procedures. The patient undergoing conscious sedation analgesia can normally respond to commands to breathe, breathe more rapidly or breathe more deeply, which usually obviates the need for ventilatory assistance or administration of antagonist agents to reverse anesthesia-induced respiratory depression. Thus, although conscious sedation patients may be at serious risk of substantial drops in blood pressure as a result of benzodi- azepine-opiate administration, they are rarely given any narcotic antagonist even when respiratory depression is evident, and less so when no respiratory distress is encountered. Yet, as described above, numerous patients have experienced severe hypotensive episodes after risk of respiratory distress has passed (e.g., hours after anesthesia is administered). Under conventional procedures these patients would not have received any antagonist while under observation, and certainly not sufficient quantities of a long-acting antagonist such as nalmefene to avoid delayed circulatory collapse.

In accordance with the invention, the long-acting pure narcotic antagonist can be administered prophylactically to every patient who has received intravenously a benzodiazepine or opiate-benzodiazepine combination. Alternatively, at the discretion of the physician, the antagonist can be administered only in those cases where it is required to counteract an observed drop in mean blood pressure.

The following Example provides a detailed illustration of the method of the present invention for safely administering benzodiazepines parenterally in combination with opiates to induce anesthesia or conscious sedation. The Example is not intended, however, to limit or restrict the scope of the invention in any way, and should not be construed as providing dosage regimens or methods of administration which must be utilized exclusively to practice the present invention.

EXAMPLE 38 patients undergoing colonoscopies were each administered 144 mg of meperidine and 7.7 mg of diazepam to induce conscious sedation. The patients were equally divided into two groups, one group receiving nalmefene intravenously subsequent to the induction of anesthesia and the other receiving a placebo.

The nalmefene group received 1 mg of nalmefene after completion of the colonoscopies. Baseline blood pressure values were taken prior to induction of anesthesia, and values were obtained again immediately before nalmefene administration ("pre-study") and again after 15 and 30 minutes. The number of patients with a reduction in mean blood pressure of greater than 10% from baseline values was determined, as reflected in the following table:

TABLE

| | Patients with >10% reduction in mean b.p. | |
|---|---|---|
| Time | Nalmefene Group (N = 19) | Placebo Group (N = 19) |
| pre-study | 7 | 5 |
| 15 min. | 5 | 12 |
| 30 min. | 4 | 8 |

The values shown in the Table indicate that at both 15 and 30 minutes, at least twice as many patients in the placebo group had greater than a 10% reduction in mean blood pressure from baseline in comparison with the nalmefene group.

In order to confirm that the effectiveness of long-acting pure narcotic antagonists in counteracting the hypotensive effects of opiate-benzodiazepine combinations is not due simply to their known activity as opiate antagonists, a further study was performed in which 209 patients receiving colonoscopies were divided into three groups. All of the patients were administered 140 mg of meperidine alone to induce anesthesia. Subsequently, the patients in the first group were administered nalmefene post procedure, the patients in the second group received naloxone and the patients in the third group received a placebo. No statistically significant differences were determined between the three groups in terms of the number of patients who experienced a reduction in mean blood pressure of more than about 10% from baseline.

It has thus been shown that there are provided methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims:

1. A method of inducing anesthesia or conscious sedation in a patient undergoing a surgical or exploratory procedure which comprises the intravenous administration to the patient of an effective amount of a benzodiazepine capable of inducing sedation or anesthesia and antegrade amnesia when injected and an effective amount of an opiate analgesic prior to the performance of said procedure, followed by the parenteral administration to the patient of from about 1.0 to about 3.0 mg of a long-acting pure narcotic antagonist to counteract an observed drop in mean blood pressure, said antagonist being administered during the time interval commencing immediately after the procedure and continuing until about 3–5 hours after administration of the benzodiazepine and opiate.

2. A method according to claim 1 wherein from about 1.5 to about 3.0 mg of said antagonist is administered to the patient.

3. A method according to claim 1 wherein said antagonist is nalmefene or naltrexone.

4. A method according to claim 3 wherein said antagonist is nalmefene.

5. A method according to claim 1 wherein said antagonist is administered as a bolus injection.

6. A method according to claim 1 wherein said antagonist is administered in two to five divided doses.

7. A method according to claim 1 wherein said antagonist is administered intravenously.

8. A method according to claim 1 wherein said benzodiazepine is diazepam, midazolam or lorazepam.

9. A method according to claim 8 wherein said benzodiazepine is diazepam.

10. A method according to claim 8 wherein said benzodiazepine is midazolam.

11. A method according to claim 1 wherein said opiate is meperidine.

12. A method according to claim 1 wherein said opiate is fentanyl.

13. A method according to claim 1 wherein conscious sedation is induced.

* * * * *